United States Patent [19]

Suddaby et al.

[11] Patent Number: 5,331,009
[45] Date of Patent: Jul. 19, 1994

[54] PHARMACEUTICAL COMPOSITIONS FOR TREATING ADRENOLEUKODYSTROPHY

[75] Inventors: Donald Suddaby, North Humberside; Keith Coupland, South Cliffe, both of United Kingdom

[73] Assignee: Croda International Plc, North Humberside, United Kingdom

[21] Appl. No.: 411,484

[22] PCT Filed: May 13, 1988

[86] PCT No.: PCT/GB88/00373
§ 371 Date: Sep. 25, 1989
§ 102(e) Date: Sep. 25, 1989

[87] PCT Pub. No.: WO89/08095
PCT Pub. Date: Sep. 8, 1989

[30] Foreign Application Priority Data

Mar. 23, 1988 [GB] United Kingdom ............... 8804188

[51] Int. Cl.⁵ ............................................. A61K 31/22
[52] U.S. Cl. ..................................... 514/549; 514/560
[58] Field of Search ............................ 514/560, 549

[56] References Cited

U.S. PATENT DOCUMENTS 4,377,526 3/1983 Fujita et al. .................... 260/424
4,442,125 4/1984 Thiele .............................. 514/560
4,843,095 6/1989 Rubin .............................. 514/560

OTHER PUBLICATIONS

Cosco, J. "The Virginia Pilot" No. 17, (1987) pp. A1 and A6.
Nassar et al., Lipids, vol. 21, No. 10 (1986) pp. 652–656.

*Primary Examiner*—Raymond J. Henley, III
*Attorney, Agent, or Firm*—Watson, Cole, Grindle & Watson

[57] ABSTRACT

A composition for the treatment of adrenoleukodystrophy comprises a mixture of erucic acid and less than 20% of C20:1, in the absence of any C24:0 and C26:0 acids (all the acids being as such or in the form of physiologically acceptable derivatives, e.g. the triglycerides). For dietary administration, the compositions are preferably mixed with a dietary supplement comprising glyceryl trioleate.

10 Claims, No Drawings

PHARMACEUTICAL COMPOSITIONS FOR TREATING ADRENOLEUKODYSTROPHY

This invention relates to the treatment of adrenoleukodystrophy (ALD) and adrenomyeloneuropathy (AMN), and to compositions useful therefor.

ALD is an inherited disease characterised by abnormally high body levels of C24 and C26 saturated fatty acids. It is believed that the reason for these high levels in ALD patients is that the body enzyme which ordinarily breaks down these acids is absent or not functioning properly. The C24 and C26 fatty acids, both saturated rand mono-unsaturated, are synthesised endogenously by the body from corresponding lower fatty acids by the same bifunctional enzyme systems. It has been suggested that, if it were possible to prevent synthesis of the (harmful) saturated fatty acids in ALD patients, then the levels of these acids should drop and so arrest further advance of the disease. With this in mind, Augusto Odone proposed treating ALD patients with a mixture of two fatty acids (in the form of their triglycerides), namely the monounsaturated C20 and C22 fatty acids, the mixture being substantially free from any similar saturated acids and containing the C20:1 and C22:1 acids in a weight ratio of 1:2, respectively. The idea was to provide the body's C24/C26-synthesising enzyme with an abundance of unsaturated acids so that corresponding C24 and C26 unsaturated acids were produced to the exclusion of any C24 and C26 saturated acids.

In the present application applicants have utilized an abbreviation for various long-chain fatty acids. As will be apparent to those of skill in the art, a long-chain fatty acid designated as C18:1 has 18 carbon atoms in the chain, with a single site of unsaturation. A C22:2 long-chain fatty acid has 22 carbons in the chain and is unsaturated at two sites. Where the term erucic acid has been used, that is the common name senoic acid. It has the formula $CH_3(CH_2)_7CH=CH(CH_2)_{11}-COOH$.

In order to test his theory, we made for Mr. Odone the triglyceride of the following mixture of fatty acids:

| | |
|---|---|
| C18:1 | traces only |
| C18:2 | traces only |
| C18:3 | traces only |
| C20:0 | traces only |
| C20:1 | 32.5% |
| C22:0 | traces only |
| C22:1 | 65.0% |
| C22:2 | traces only |
| C24:0 | zero |
| C24:1 | 1% maximum |
| C26:0 | zero |

The total amount of all trace components was no more than 1.5% of the total fatty acid content of the mixture.

When this composition was administered to two ALD patients in their diets, the results were dramatic. Over a period of three weeks, their C24:0 and C26:0 acid levels in total plasma and sphingomyelin were reduced to normal. Evidently, therefore, this is a highly successful way of reducing the damagingly high acid levels in ALD patients and is indeed a major breakthrough in the treatment of the disease.

Unfortunately, however, the manufacture of the above mixture of acids, to exactly the composition indicated, is a long and difficult procedure and, as a result, is very expensive. However, in accordance with a feature of the present invention, it has now been found that the presence of such high levels of C20:1 in the compositions is unnecesary and that it is the C22:1 component which is by far the more important. Indeed, the C20:1 component can be omitted completely. In this way, the compositions can be made more easily and economically.

According to a feature of the present invention, therefore, there is provided a composition for the treatment of ALD and related diseases, which comprises erucic acid (C22:1) and no more than 20% of C20:1, in the substantial absence of C24:0 and C26:0 acids, the composition being in a form suitable for administration to the patient. Normally, the acids in the composition will be in the form of their triglycerides. For simplicity, we refer hereafter to the acids in the compositions, but intend thereby to include reference to physiologically acceptable derivatives, e.g. the triglycerides, as the context determines.

In the treatment of ALD patients, great care has to be taken over their diet because, of course, foodstuffs frequently contain oils and fatty acids. In order to avoid any risk of ingestion of the harmful C24:0 and C26:0 acids, it is known to use foodstuffs which do not contain long chain fatty acids, and to give the patient a controlled supplement containing acceptable safe fatty acids and oils which are essential to the body's requirements. Work carried out by Dr. W. B. Rizzo et al. (Neurology 36 (1986) 357) and by Dr. H. W. Moser et al. (Ann. Neurol. 21, 1987) has shown that the administration of oleic acid (C18:1) to ALD patients is generally therapeutically advantageous. In particular, if very long chain fatty acids are omitted from the diet and glyceryl trioleate used alone to supply the body needs, reductions can occur in the C26:0 body levels. Thus, glyceryl trioleate oil is a highly suitable dietary supplement for ALD patients.

In accordance with a feature of the present invention, therefore, the erucic acid compositions of the invention can be mixed with a dietary supplement, preferably oleic acid triglyceride, so that the composition when administered supplies not only the normal fatty acid body requirements but also provides the vital therapeutic effects of erucic acid (in the absence of C24:0 and C26:0). The amounts of erucic acid triglyceride in such compositions may be quite low, e.g. from 10 to 25%, depending (among other things) on the required dosage of oleic acid triglyceride. The minimum is the least amount which gives the desired therapeutic effect.

When the compositions of the invention do not contain supplementary amounts of oleic acid triglyceride (or another such supplement), they will normally comprise at least 50% erucic acid and, most preferably, over 90% erucic acid. The other components of the compositions will be substances which can safely be given to ALD patients. These may include other acids, e.g. the C:20 acids and C24:1 which is advantageously and preferably present in amounts up to at least 3%. Other substances which may be present are those which are incidental or present as a consequence of the way in which the composition has been made. There may of course be deliberate additions of therapeutic or other substances as directed by the physician. Also, the compositions may of course comprise conventional diluents, carriers and excipients (provided they are safe for ALD patients). The compositions will normally be in a form suitable for dietary administration, but may be otherwise formulated if desired.

One example of a high-erucic content composition of the present invention (in which the acids are present as their respective triglycerides) is as follows:

| C18:1 | traces only |
| C18:2 | traces only |
| C18:3 | traces only |
| C20:0 | 0.2% maximum |
| C20:1 | 1.0–3.5% |
| C20:2 | traces only |
| C22:0 | 0.2% maximum |
| C22:1 | 93.5–95% |
| C22:2 | traces only |
| C24:0 | zero |
| C24:1 | 1.0 to 2.5% |
| C26:0 | zero |

It has been found that when ALD patients are treated with the erucic acid compositions of the invention, these compositions are as effective as the mixed C20'/C22' acid composition previously used. The invention thus includes a method of treatment of ALD and related diseases which comprises administering to the patient a composition of the present invention.

In order to make the compositions of the invention, and in particular the erucic acid component thereof (and other acids as may be present), we fractionally distil the fatty acids or fatty acid methyl esters obtained by the hydrolysis or transesterification of natural oils such as high erucic rape oil or oils obtained from other Brassica seeds containing high percentages of erucic acid. Essentially, the process involves treatments with urea to remove saturated acids, fractional distillations to purify the erucic acid, and finally conversion to, say, the triglyceride and subsequent purification thereof. The invention further includes a process for the preparation of a composition of the invention which comprises treating an erucic acid-rich fatty acid obtained by the fractional distillation of the fatty acids, or fatty acid methyl esters resulting from the hydrolysis or transesterification of a natural oil, with urea (or the like) to remove saturated acids, fractional distillations, and optional conversion to a derivative thereof, to provide a product consisting essentially of erucic acid (optionally as a derivative) and being free from C24:0 and C26:0 acids.

The following Example is given by way of illustration only.

EXAMPLE

Reagents 4150 gm 92% C22:1 methyl ester
3115 ml ethanol (99 grade)
935 gm urea+a further 180 gm urea dissolved in 60 ml ethanol.

The gas-liquid chromatographic composition of the plant distilled methyl erucate starting material was:

| C18:0 | 0.10% |
| C18:1 | 0.09% |
| C18:2 | 0.10% |
| C20:0 | 0.40% |
| C20:1 | 2.69% |
| C22:0 | 1.15% |
| C22:1 | 91.39% |
| C22:2 | 1.17% |
| C24:0 | 0.25% |

| -continued | |
|---|---|
| C24:1 | 2.45% |

The C26:0 acid was left behind with the residues.

The above methyl erucate material and the 3115 ml ethanol and the 935 gm of urea were charged cold into a 10 liter flange-necked flask fitted with a water-cooled reflux condenser, stirrer, thermometer and a temperature control probe. The mixture was heated to 82° C. and refluxed for 2½ hours with stirring.

The suspension was cooled to 70° C. and a boiling solution of gm urea in 600 ml ethanol added rapidly to the suspension and the mixture again refluxed for a further 1½ hours.

This addition of urea solution was found necessary to remove any small percentages of saturated acid esters that had escaped inclusion in the first formed urea adduct.

The urea adduct of the saturated acids came down as a crystalline solid.

1. The suspension was allowed to cool over night to ambient temperature and the urea adduct filtered off in a Buchner funnel. The filtrate was kept in a refrigerator at +2° C. for 12 hours and again filtered through a Buchner funnel.

The filtrate was then stripped under water pump vacuum at 34° C. and finally at 64° C. to remove the ethanol. During the evaporation of the ethanol solution more urea and urea complex were precipitated and the suspension was cooled overnight at +2° C. and re-filtered.

The saturate-free ester was then washed three times with one liter of distilled water at 80° C. the first wash containing a few ccs dilute HCl.

The final wash water was of pH 5.

2. The saturate-free methyl ester was then saponified and the potassium soaps hydrolysed to the free acid with aqueous sulphuric acid as exemplified by the following batch.

| Reagents | |
|---|---|
| Saturate-free methyl erucate | 2400 gm |
| Potassium hydroxide pellets | 600 gm |
| Distilled Water | 4500 ml |

The methyl ester, potassium hydroxide and distilled water were charged into a 10 liter flask fitted with a stirrer, water cooled reflux condenser, thermometer and temperature control probe. The charge was refluxed with stirring for half an hour and the temperature reduced to a maximum of 95° C. Above this temperature excessive foaming results. After a period of 4 to 6 hours the soaps form an opaque gel which is very viscous and a heavy duty stirrer is required.

After about 12 hours the gel becomes translucent and 1 liter of hot distilled water was added and stirring and heating at 95° C. continued for 12 hours after this point.

The translucent gel is then cooled to 60° C. and with stirring; 530 gm concentrated sulphuric acid diluted 1:1 with distilled water was added gradually.

The gel is transformed into a very lumpy soap and further additions of 2×200 gm concentrated sulphuric acid diluted to 1:1 with distilled water were made and heating continued at reflux temperature of 102° C. for four hours, after which the soap became more mobile and eventually hydrolysed into a pale yellow oil/water emulsion.

Heating and stirring were continued for a further six hours when, on stopping the stirrer, the emulsion rapidly separates into two sharply defined phases.

The two phase system was allowed to cool to 40° C. and the lower aqueous phase run off.

The upper layer of erucic acid was washed 3 times with 1 liter portions of distilled water at 50° C. and the final wash water was of pH not less than 4.

The crude erucic acid was dried under high vacuum at 60° C. max.

3. The crude erucic acid was fractionally distilled under a vacuum of 0.6 to 0.2 millibars. The first liter of foreruns was quite a deep yellow colour and was rejected, but a further 4 fractions collected between 226° C. and 242° C. were of excellent colour and were combined. Acid values of the bulk and gas-liquid chromatographic composition were obtained.

4. The triglyceride of the distilled acid was prepared using a stoichiometric quantity of glycerol at 175° C.–180° C. under vacuum using $SnCl_2.2H_2O$ as a catalyst. The vacuum used and length of reaction were adjusted to give the best coloured product and to eliminate the formation of monoglycerides which are only slightly soluble in ether and also give rise to emulsions during the refining process. The optimum conditions are given in the following batch reaction:

| Reagents | |
|---|---|
| 95% Pure Erucic Acid | 2995 gm |
| Glycerol B.P. | 270.5 gm |
| $SnCl_2.2H_2O$ | 5.4 gm (0.008 mole per 100 gm fatty acid) |

The reagents were charged into a 10 liter flask fitted with a stirrer, thermometer, temperature control probe and a vertical water cooled reflux condenser.

The vertical reflux condenser was fitted with a still head with thermometer leading to another water cooled condenser leading to a three-necked flask immersed in a solid carbon dioxide/ethanol bath. One neck of this flask was fitted with a Pirani vacuum gauge and the other neck connected to the final solid carbon dioxide/ethanol pump trap.

The charge was then heated to 75° C. with stirring and purged with nitrogen for half an hour. The charge was then heated to 175° C. with stirring at a vacuum of 5 millimeters.

The charge is at first heterogeneous, but at 175° C. water is given off due to the reaction and any glycerol or fatty acid which is steam distilled is condensed by the first 3 inches (7.6 cm) of the reflux condenser and the temperature at the still head should not rise above 30° C.

After about 8 hours' reaction time, the charge clarifies and only a little water vapour bubbles off. The vacuum is then reduced to 0.2 millibars and the reaction continued for a total time of 24 hours. The charge was then cooled to 80° C. and an acid value determined. The acid value is usually between 10 and 18 at this stage.

The stoichiometric amount of glycerol to convert the free fatty acid present to triglyceride is then added and the procedure repeated, i.e. 8 hours at 5 millimeters vacuum and then 24 hours' total heating time at 0.2 millibars. The acid value is by this stage less than 1.

The cooled charge is then washed three times with 1 liter portions of distilled water at 80° C. The washed triglyceride was then taken into ether and washed with 1 liter of distilled water at 30° C. containing the requisite amount of 0.5N sodium hydroxide solution to neutralise the final acid value of the crude triglyceride.

Finally the ether solution was washed with 2 further liters of distilled water, and then dried over anhydrous sodium sulphate.

The ether is evaporated off using a water bath to provide heat and initially a water vacuum pump with a nitrogen bleed.

When the ether content is below 500 ppm, the water pump is changed to a high vacuum pump fitted with an efficient solid carbon dioxide/ethanol trap. The nitrogen bleed is still used and heat supplied by a heating mantle at 80° C. for 3 to 4 hours by which time the ether content is below 20 ppm.

The triglyceride is then filtered warm through a Buchner funnel using a celite pad.

The acid value and the iodine value of the filtered triglyceride are determined and the gas-liquid chromotographic composition determined on the methyl ester obtained by transmethylation of the triglyceride. The absence of mono- and di-glycerides is confirmed by thin layer chromatography.

1. Results
After urea treatment
The gas-liquid chromatographic composition was:

| C18:0 | zero |
|---|---|
| C18:1 | 0.15% |
| C18:2 | 0.07% |
| C18:3 | zero |
| C20:0 | 0.08% |
| C20:1 | 1.84% |
| C20:2 | 0.18% |
| C22:0 | 0.12% |
| C22:1 | 93.12% |
| C22:2 | 1.65% |
| C24:0 | zero |
| C24:1 | 2.79% |
| C26:0 | zero |

2. After saponification with aqueous potassium hydroxide and hydrolysis with sulphuric acid followed by fractional distillation and rejection of foreruns:
Gas-liquid chromatographic composition

| C18:0 | zero |
|---|---|
| C18:1 | 0.09% |
| C18:2 | zero |
| C20:0 | 0.08% |
| C20:1 | 1.80% |
| C20:2 | 0.12% |
| C22:0 | 0.11% |
| C22:1 | 93.9% |
| C22:2 | 1.55% |
| C24:0 | zero |
| C24:1 | 2.35% |
| C26:0 | zero |

8.96 kg of urea treated methyl ester gave 6.35 kg ~94% C22:1 acid of excellent color.

3. Preparation of Triglyceride
6.35 kg 94% C22:1 acid gave a yield of 6.05 kg triglyceride acid value = 0.5, iodine value = 74.2.
Gas-liquid chromatographic composition of triglyceride:

| C18:0 | zero |
|---|---|
| C18:1 | 0.05% |
| C18:2 | zero |
| C18:3 | zero |
| C20:0 | 0.07% |
| C20:1 | 1.70% |
| C20:2 | 0.16% |
| C22:0 | 0.10% |
| C22:1 | 94.20% |
| C22:2 | 1.52% |
| C24:0 | zero |

| | |
|---|---|
| C24:1 | 2.20% |
| C26:0 | zero |
| Absence of mono- and di-glycerides confirmed by thin layer chromatography. | |
| Color Pale Golden Yellow Oil commences to crystallise at 27° C. | |

We have described above Mr. Augusto Odone's idea of treating ALD by providing in the body an abundance of monounsaturated (over saturated) acids so that the enzyme(s) synthesising C24 and C26 acids would produce only the monounsaturated C24 and C26 acids. This treatment can also be used for AMN and for symptomatic female heterozygotes (carriers who sometimes show symptoms).

It is possible to omit the saponification of the methyl ester with potassium hydroxide and the subsequent hydrolysis of the potassium salts to erucic acid by a synthesis of the triglyceride direct from the methyl ester, after removal of the saturated acids by urea, by transesterification of this methyl ester with glycerol by heating the stoichiometric quantites of glycerol and methyl ester in the presence of catalysts such as sodium methoxide, organo-tin catalysts or organo-titanium catalyst.

The solvent used in the purification of the triglyceride may be changed from diethyl ether to less hazardous solvents such as n-hexane.

Furthermore, the synthesis of the triglyceride can be carried out by the use of other low alkyl analogues of methanol as in the methyl ester, by esters such as ethyl erucate.

A further purification of the final triglyceride can be carried out by the use of liquid column chromatography.

We claim:

1. A method for treating adrenoleukodystrophy, which comprises administering a pharmacologically effective amount of a composition which includes an effective amount of C22:1 long-chain fatty acid and no more than about 20 percent of C20:1 long-chain fatty acid, the ratios of said C22:1 to C20:1 acids being substantially greater than 2:1, said composition being substantially free of saturated fatty acids having 24 and 26 carbon atoms.

2. A method as claimed in claim 1, wherein said C22:1 acid is erucic acid.

3. A method as claimed in claim 2, wherein said erucic acid is in the form of its triglyceride derivative.

4. A method as claimed in claim 2, in which the composition comprises at least 90% erucic acid.

5. A method as claimed in claim 1, in which the composition comprises no more than 4% of said C20:1 acid.

6. A method as claimed in claim 1, in which the composition further includes a physiologically acceptable diluent, carrier or excipient.

7. A method as claimed in claim 1, in which the composition further includes an oleic acid triglyceride.

8. A method as claimed in claim 1, in which the ratio of said C22:1 to C20:1 acids is greater than 25:1.

9. A method as claimed in claim 8, in which said ratio is greater than 50:1.

10. A method as claimed in claim 9, in which said ratio is greater than 90:1.

* * * * *

UNITED STATES PATENT AND TRADEMARK OFFICE
Certificate

Patent No. 5,331,009                                                                             Patented: July 19, 1994

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Donald Suddaby, North Humbersid, United Kingdom; Keith Coupland, South Cliffe, United Kingdom; and Augusto Odone, Fairfax, Virginia.

Signed and Sealed this Third Day of November, 1998.

MARIANNE M. CINTINS
                                                                                                                                Art Unit 1614